(12) United States Patent
Ogawa et al.

(10) Patent No.: US 7,488,071 B2
(45) Date of Patent: Feb. 10, 2009

(54) OPHTHALMOLOGIC IMAGE RECORDING APPARATUS, OPHTHALMOLOGIC IMAGE RECORDING METHOD, AND OPHTHALMOLOGIC IMAGE RECORDING PROGRAM

(75) Inventors: Tetsuji Ogawa, Utsunomiya (JP); Shigeaki Ono, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 251 days.

(21) Appl. No.: 10/596,986

(22) PCT Filed: Jul. 14, 2005

(86) PCT No.: PCT/JP2005/013440

§ 371 (c)(1),
(2), (4) Date: Jul. 3, 2006

(87) PCT Pub. No.: WO2006/009237

PCT Pub. Date: Jan. 26, 2006

(65) Prior Publication Data

US 2007/0126984 A1 Jun. 7, 2007

(30) Foreign Application Priority Data

Jul. 20, 2004 (JP) .............................. 2004-211688

(51) Int. Cl.
*A61B 3/14* (2006.01)
*A61B 3/00* (2006.01)

(52) U.S. Cl. ........................................ 351/206; 351/246

(58) Field of Classification Search ......... 351/205–206, 351/210, 246
See application file for complete search history.

(56) References Cited

U.S. PATENT DOCUMENTS

| 5,530,494 A | 6/1996 | Ogawa et al. |
| 5,894,337 A | 4/1999 | Okinishi et al. |
| 6,158,864 A | 12/2000 | Masuda et al. |
| 6,192,269 B1 | 2/2001 | Okumura et al. |

(Continued)

FOREIGN PATENT DOCUMENTS

JP 2002-238860 8/2002

(Continued)

OTHER PUBLICATIONS

Oct. 4, 2005 International Search Report in PCT/JP2005/013440.

(Continued)

*Primary Examiner*—Scott J Sugarman
*Assistant Examiner*—Dawayne A Pinkney
(74) *Attorney, Agent, or Firm*—Fitzpatrick, Cella, Harper & Scinto

(57) ABSTRACT

A plurality of sensed images of an eye to be examined and a plurality of time information at image sensing are acquired. A plurality of information correlate with image, each of which including at least the time information, at the image sensing are acquired. A group of the images of the eye to be examined and a group of the information correlate with image sensing are correlated with each other based on the time information at the image sensing and the time information included in the information correlate with image sensing, thereby recording an image of the eye to be examined and information correlate with image sensing which are correlated with each other.

6 Claims, 10 Drawing Sheets

U.S. PATENT DOCUMENTS

| | | |
|---|---|---|
| 6,327,375 B1 | 12/2001 | Matsumoto et al. |
| 6,332,683 B1 | 12/2001 | Ono et al. |
| 6,337,993 B1 | 1/2002 | Kishida et al. |
| 6,535,757 B2 | 3/2003 | Ono |
| 6,569,104 B2 | 5/2003 | Ono et al. |
| 6,644,809 B2 | 11/2003 | Ogawa |
| 6,773,109 B2 * | 8/2004 | Ichikawa et al. ............ 351/206 |
| 6,834,202 B2 | 12/2004 | Ono |
| 2001/0028439 A1 * | 10/2001 | Itoh .......................... 351/206 |
| 2002/0059301 A1 * | 5/2002 | Hayashi et al. .......... 707/104.1 |
| 2002/0113939 A1 | 8/2002 | Kitamura ................... 351/200 |
| 2004/0008322 A1 | 1/2004 | Ogawa |

FOREIGN PATENT DOCUMENTS

| | | |
|---|---|---|
| JP | 2004-105594 | 4/2004 |

OTHER PUBLICATIONS

Oct. 4, 2005 Written Opinion in PCT/JP2005/013440.

* cited by examiner

OPHTHALMOLOGIC IMAGE RECORDING APPARATUS, OPHTHALMOLOGIC IMAGE RECORDING METHOD, AND OPHTHALMOLOGIC IMAGE RECORDING PROGRAM

TECHNICAL FIELD

The present invention relates to an ophthalmologic image recording apparatus connected with, for example, an eye fundus camera for sensing a fundus of an eye to be examined, which is used in an ophthalmologic office, for a group examination, or the like, an ophthalmologic image recording method, and an ophthalmologic image recording program.

BACKGROUND ART

For example, an image filing system for an eye fundus camera has been known as an ophthalmologic image recording apparatus.

The mainstream of the system is a system for capturing a still image of an eye to be examined, in a recording medium in synchronization with an analog video signal used in a camera including an analog video output terminal.

In recent years, because it is easy to digitize, general digital cameras have been used in a film compartment of the eye fundus camera. In particular, the reason why a single-lens reflex type digital camera is used is that remote image sensing from the eye fundus camera is possible and it has high compatibility with conventional film type cameras and resolution sufficient for an ophthalmologic diagnostic image.

In order to be able to easily store, retrieve, and view images, the images can be transferred from the general digital camera to a personal computer through memory cards, cables, or the like.

On the other hand, the image filing system for the eye fundus camera requires information correlating with image sensing, such as (1) "when", (2) "where image sensing is performed", (3) "who", and (4) "either eye", in addition to the image. Therefore, in order to achieve this, there has been known that the information correlating with image sensing is directly inputted to the personal computer or the information correlating with image sensing is outputted from the eye fundus camera and then stored in correlation with the image of the eye to be examined.

An apparatus for automatically reading the information correlating with image sensing, such as eyes to be sensed (left and right) from an image sensing device has been known an example of such a technique (see Patent Document of JP 2002-238860 A).

However, when the image of the eye to be examined and the information correlating with image sensing are surely correlated with each other to improve the reliability of the apparatus, it is necessary to substantially simultaneously obtain the image and the information correlating with image sensing. This can be achieved without problems because the image can be promptly obtained in a conventional mode for capturing the video signal.

However, in the case of image sensing using a generally used digital camera, image generation and mass data transfer are performed in the digital camera, so image acquisition requires considerable time. In order to avoid this, a method of inhibiting next image sensing until after the completion of the image acquisition is expected. In this case, it is impossible to perform image sensing with short intervals, such as fluorescent image sensing. In order to deal with the image sensing with short intervals, when the information correlating with image sensing is added to only a first image of successively sensed images and other images are not correlated with the information correlating with image sensing, a plurality of images, each of which does not include the information correlating with image sensing exist.

When the general digital camera is used in the film compartment of the eye fundus camera, the remote image sensing from the eye fundus camera is normally performed. However, when image sensing operation is performed by using an image sensing switch provided in the main body of the eye fundus digital camera, an image other than images sensed by the eye fundus camera (improper image which is not an eye fundus picture) generates.

Even when the image generation, the image transfer, or the like is caused by noise which an operator does not expect, the same occurs.

When such concern is taken into account, it is hard to surely correlate the image of the eye to be examined and the information correlating with image sensing while avoiding an improper image and to perform continuous image sensing at an image sense interval shorter than an image transfer time.

DISCLOSURE OF THE INVENTION

The present invention has been made in view of the above problems, and therefore provides an ophthalmologic image recording apparatus capable of removing an improper image which is not an eye fundus picture and correlating each image with information correlate with image sensing.

According to an aspect of the invention, an ophthalmologic image recording apparatus includes: a first acquiring means for acquiring a plurality of sensed images of an eye to be examined and a plurality of time information at image sensing; a second acquiring means for acquiring a plurality of information correlate with image sensing, each of which including at least the time information, at the image sensing; control means for correlating a group of the images of the eye to be examined with a group of the information correlate with image sensing; and recording means for recording an image of the eye to be examined and information correlate with image sensing which are correlated with each other, and in the ophthalmologic image recording apparatus, the control means correlates the group of the images of the eye to be examined with the group of the information correlate with image based on the time information at the image sensing and the time information included in the information correlate with image sensing.

BRIEF DESCRIPTION OF THE DRAWINGS

The accompanying drawings, which are incorporated in and constitute a part of the specification, illustrate embodiments of the invention, and together with the description, serve to explain the principles of the invention.

BEST MODE FOR CARRYING OUT THE INVENTION

Preferred embodiment(s) of the present invention will be described in detail in accordance with the accompanying drawings.

Hereinafter, an embodiment of the present invention will be described in detail with reference to the drawings.

Figure 1:
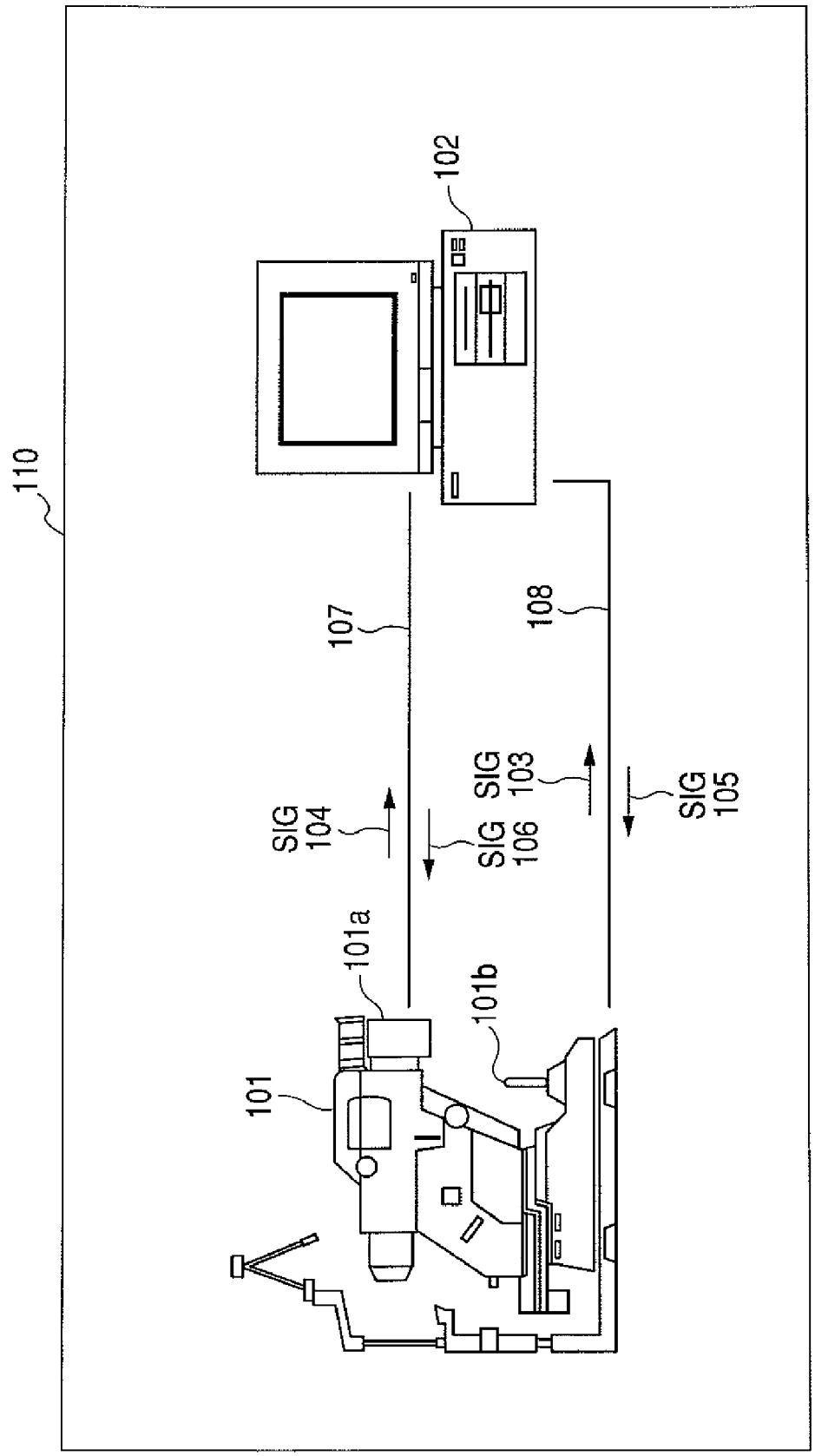
FIG. 1 is a structural view showing a filing system using a mydriatic type eye fundus camera.

FIG. 1 shows a structure of a filing system using a mydriatic type eye fundus camera, which is one of ophthalmologic image recording apparatuses. A filing system 110 includes a mydriatic type eye fundus camera 101 and a personal computer 102 for file management. The mydriatic type eye fundus camera 101 includes a digital camera 101a which has a photo sensor such as a CCD and that generates a digital image and an image sensing start switch 101b. Two communication paths are used between the mydriatic type eye fundus camera 101 and the personal computer 102. Image data Sig104 is outputted from the digital camera 101a to a communication path 107 and a signal Sig106 is outputted from the personal computer 102 to the communication path 107 to detect a state of the digital camera 101a. Information correlating with image sensing Sig103 is outputted from the mydriatic type eye fundus camera 101 to a communication path 108 and an image sense enable signal Sig105 indicating that image sensing operation is an enable state is outputted from the personal computer 102 to the communication path 108.

Figure 2:
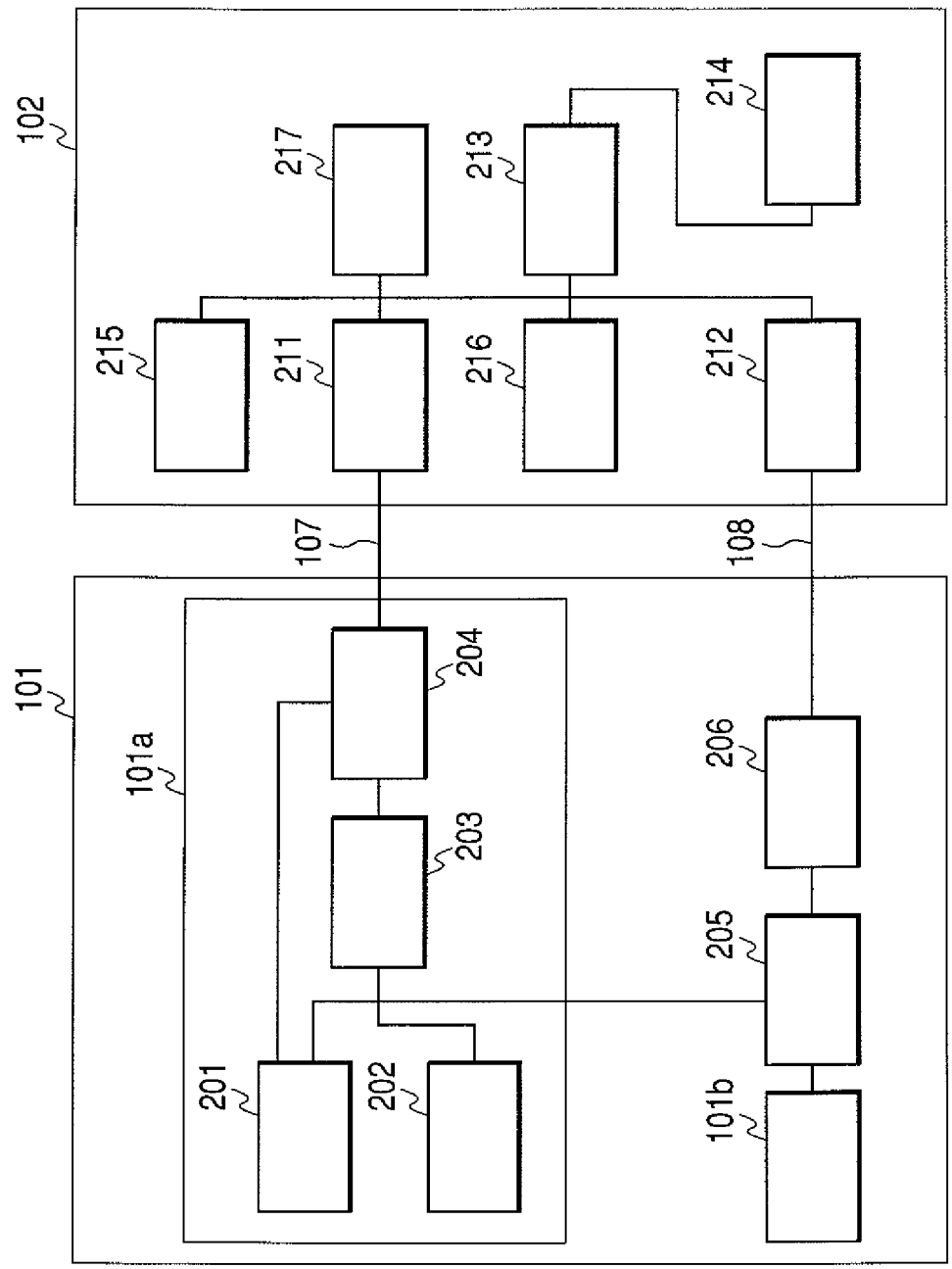
FIG. 2 is a structural diagram showing detailed parts in an embodiment of the present invention.

Next, a structure of detailed parts in the present invention will be described. FIG. 2 shows the structure of the detailed parts in an embodiment of the present invention. The mydriatic type eye fundus camera 101 includes the digital camera 101a, the image sensing start switch 101b, an eye fundus camera controlling part 205 for controlling the mydriatic type eye fundus camera 101, and an image sensing information management unit 206 for the mydriatic type eye fundus camera 101. The digital camera 101a includes a photo sensor 201 such as a CCD, an image sensing switch 202 for the digital camera 101a, a digital camera controlling part 203 for controlling the digital camera 101a, and an image data generation unit 204 for generating image data from the digital camera 101a.

The personal computer 102 includes an image data storing part 211 for storing the image data outputted from the image data generation unit 204, an image-sensing-correlation-information storing part 212 for storing the information correlating with image sensing, which is outputted from the image sensing information management unit 206, an image file creating part 213 for creating an image file to which the information correlating with image sensing is added, based on the image data and the information correlating with image sensing, a file storing unit 214 for storing the image file to which the information correlating with image sensing is added, an image sensing condition information inputting part 215 for inputting image sensing condition information such as a patient's name and an image sensing region, a calculation processing part 216 for controlling the personal computer 102, and an alarm generation means 217 for generating an alarm when an improper image is recognized.

In the structure of the filing system 110 described above, a rough flow from the selection of a patient to the storage of the image will be described. First, when a patient to be sensed is determined, the personal computer 102 performs the selection of the patient, the checking of patient information, and the like using the image sensing condition information inputting part 215. Next, when the patient information is determined, in order to enable the image sensing, the image sense enable signal Sig105 is outputted through the communication path 108. The outputted image sense enable signal Sig105 allows the operation of the mydriatic type eye fundus camera 101. When alignment operation and focusing operation are performed on the eye to be examined to determine the image sensing region, the operator operates the image sensing start switch 101b of the mydriatic type eye fundus camera 101 to perform the image sensing of the eye fundus. After the optical path changing and the like are performed, the mydriatic type eye fundus camera 101 causes a strobe scope light source which is not shown to emit light and simultaneously issues a remote image sense signal to the digital camera 101a. A fundus image of the eye to be examined which is illuminated by the strobe scope light source is formed on the photo sensor 201 of the digital camera 101a through an optical system which is not shown. The digital camera controlling part 203 receives the remote image sense signal and causes the image data generation unit 204 to execute the generation of image data to which an image generation time is added. After the generation of the image data is completed, the personal computer 102 detects the generation of the image data using the signal Sig106 outputted through the communication path 107. After the completion of the generation, the digital camera controlling part 203 performs the image data transfer in response to an image transfer request from the personal computer 102. The personal computer 102 starts the storage of the image data Sig104 received through the communication path 107 in the image data storing part 211.

In addition to this, after the completion of the image sensing, the mydriatic type eye fundus camera 101 acquires the information correlating with image sensing, including an image sense time, a left or right eye, an image sense angle of field, an image sense light intensity, and timer information and causes the image sensing information management unit 206 to record information correlating with image sensing. The information correlating with image sensing which is recorded in the image sensing information management unit 206 is outputted as the information correlating with image sensing Sig103. The personal computer 102 causes the image-sensing-correlation-information storing part 212 to store the outputted information correlating with image sensing Sig103. When all data are stored in the image data storing part 211 and the image-sensing-correlation-information storing part 212, the calculation processing part 216 compares the generation time added to the image data with the image sense time included in the information correlating with image sensing. When a difference between the two time information is within an allowable range, the image file creating part 213 is directed to create a file. The image file creating part 213 creates a new file in which the information correlating with image sensing is added to the image data. After the file creation is completed, the created file is stored in the image file storing unit 214. The above-mentioned operation is the rough flow from the selection of the patient to the storage of the image. Next, the present invention will be described in detail with reference to the timing charts.

Figure 3:
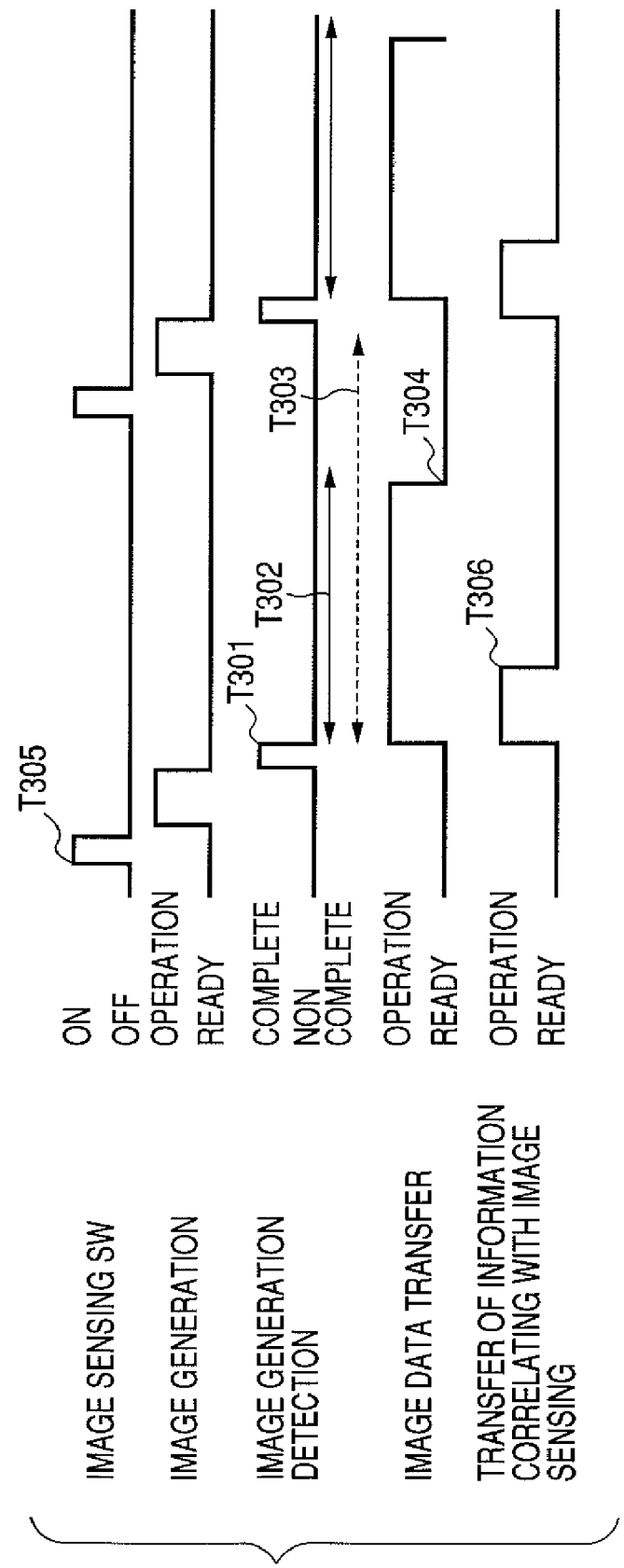
FIG. 3 is a timing chart showing image sensing operation.

FIG. 3 is a timing chart showing detailed operating procedures with respect to image sensing, data transfer, and the like in this system. First, when the operator presses the image sensing start switch 101b, an image sense switch signal changes to an ON state. After that, the mydriatic type eye fundus camera 101 performs operation such as optical path changing and then causes the strobe scope light source which is not shown to emit light. Then, the image of the eye to be examined is formed on the sensor 201 of the digital camera. The eye fundus camera 101 simultaneously transmits the remote image sense signal to the digital camera 101a. Therefore, the digital camera 101a starts the image generation operation shown in FIG. 3. The personal computer 102 periodically detects an image generation state through the communication path 107, so the completion of the image generation is detected in response to the completion of the image generation in the digital camera 101a. The calculation processing part 216 of the personal computer 102 stores a detection time at a timing T301 of the completion of image generation detection and simultaneously starts a timer T302 for monitoring subsequent data transfer. Note that T303 indicated by a dotted line denotes a timeout period of T302. Next, the calculation processing part 216 requests the digital camera 101a to transfer the generated image data. Then, the image data transfer shown in FIG. 3 changes to an operation state. On the other hand, when the operation after the image sensing is completed, the image sensing information management unit 206 of the mydriatic type eye fundus camera 101 acquires and records the information correlating with image sensing, including image sense time information acquired at T305 when the image sensing start switch 101b is pressed. When the storage of the information correlating with image sensing is completed, the image sensing information management unit 206 starts the transfer of the information correlating with image sensing to the image-sensing-correlation-information storing part 212 of the personal computer 102 at a timing of T306. The calculation processing part 216 of the personal computer 102 stores a transfer start time. After that, the calculation processing part 216 constantly monitors the transfer states of the two pieces of data and stops the timer T302 at a time T304 when the transfer of both the image data and the information correlating with image sensing is completed (transfer complete time of the image data in this embodiment). In FIG. 3, the transfer of the image data and the information correlating with image sensing is normally completed within the timeout period T303, so the acquired time information are checked without alarm operation with respect to the timeout. It is checked that a difference between the time information acquired when the T301 is detected and the generation time information included in the image information acquired at T304 is within a predetermined value. It is checked that a difference between time information acquired when the start of transfer of the information correlating with image sensing is detected and time information included in the information correlating with image sensing is within a predetermined value. It is checked that a difference between the time information with respect to the image data and time information with respect to the information correlating with image sensing is within a predetermined value, so it is recognized that the image data and the information correlating with image sensing are data generated at the same image sensing. In response to this, the image file creating part 213 creates an image file to which the information correlating with image sensing is added. The same operation is performed for second image sensing shown in FIG. 3. As described above in FIG. 3, the image data is checked using both the detection time of the image generation and time information included in the image data. It is possible to compare either information with the time information with respect to the information correlating with image sensing. Although the example in which the time information is included in the image data has been described, a digital camera capable of independently acquiring or detecting only the time information may be used. With respect to the information correlating with image sensing, the checking is performed using both the time information acquired when the information correlating with image sensing is detected and the time information included in the information correlating with image sensing. It is possible to compare either information with the time information with respect to the image data. In FIG. 3, the example in which the start of transfer of the image sensing information is later than the detection timing of the image generation has been described. However, in the case where the start of transfer of the image sensing information is earlier than the image generation, even when the timer T302 is started based on the transfer of the image sensing information, the same effect is obtained. Described in FIG. 3 is the case in which the operation is normally completed. Here, when the timer T302 exceeds the timeout period T303 because of the failure of the digital camera 101a, the disconnection of the communication path 107 for the image data and the generation of noise therein, the inner failure of the mydriatic type eye fundus camera 101, and the disconnection of the communication path 108 and the generation of noise therein, the calculation processing part 216 directs the alarm generation means 217 to generate an alarm. An alarm generating method will be described in detail later.

Figure 4:
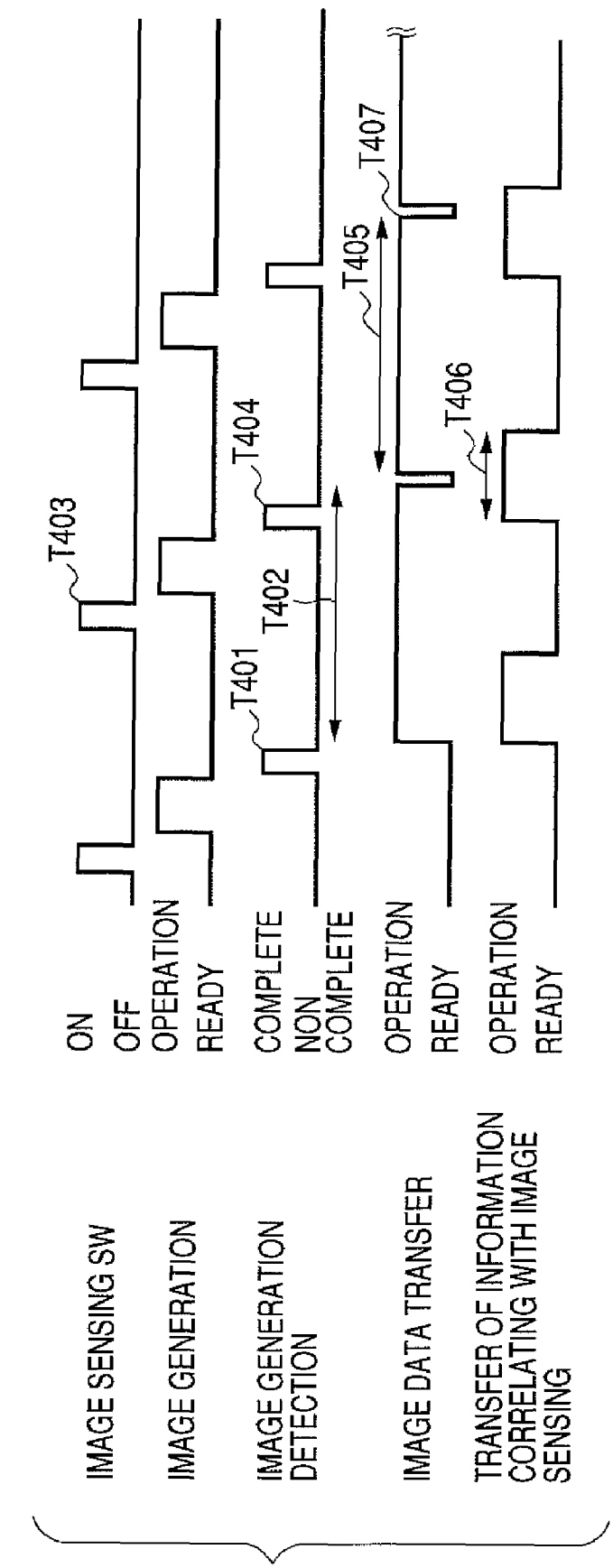
FIG. 4 is a timing chart showing image sensing operation.
Figure 8:
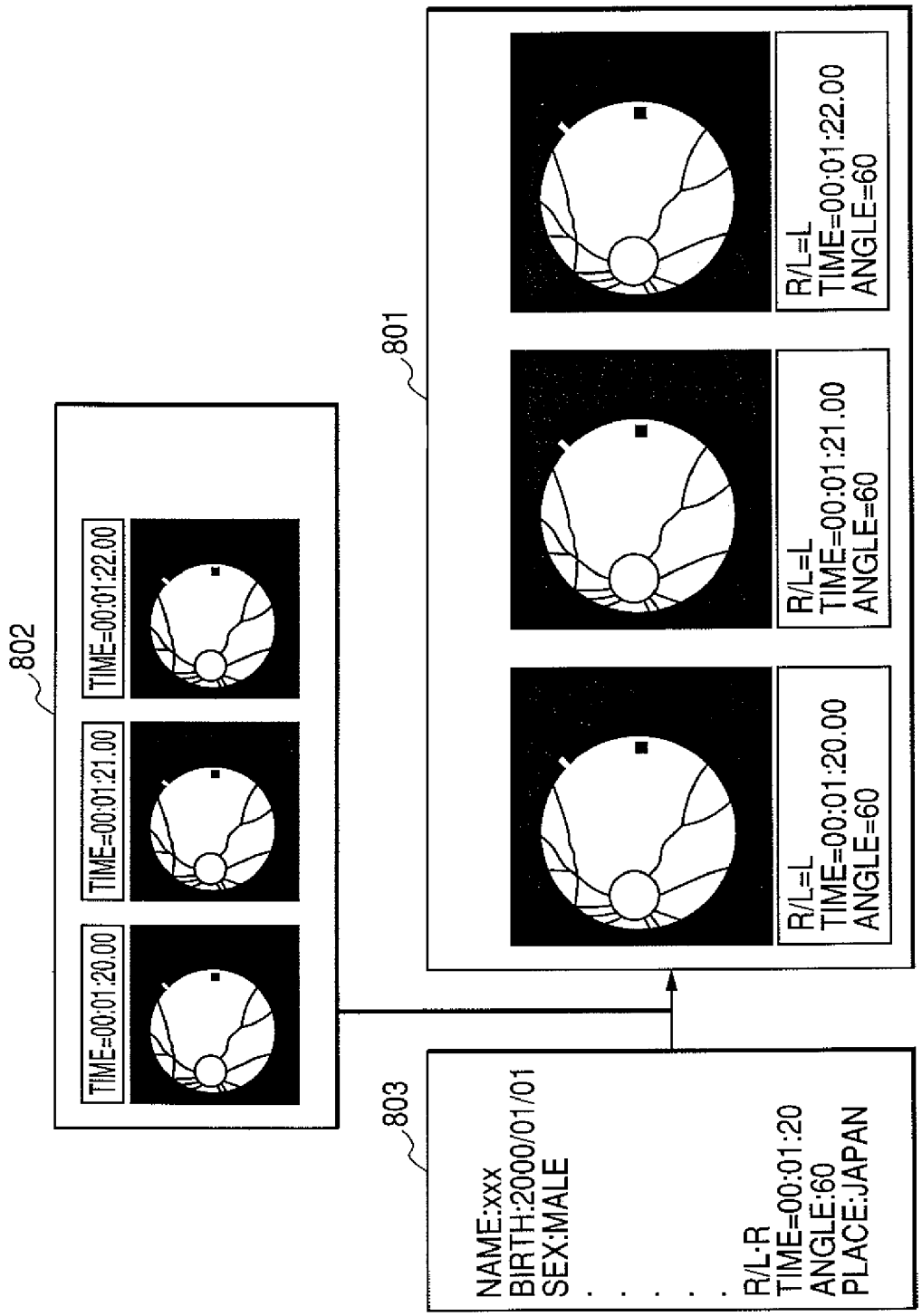
FIG. 8 is a view showing transfer data and displayed images.

FIG. 4 is a timing chart showing continuous image sensing such as fluorescent image sensing. When the mydriatic type eye fundus camera 101 is operated to start image sensing, the calculation processing part 216 detects the image generation at a timing T401 and starts a timer of T402. Because of the continuous image sensing, next image sensing is started at a timing T403 during the transfer of first image data. Therefore, the calculation processing part 216 starts a second timer T406 at a time T404 when next image generation is detected and simultaneously stores a detection time of T404. The second timer T406 is a timer for monitoring a transfer state of the information correlating with image sensing and used to detect a timeout error of the information correlating with image sensing. Next, when the transfer of the image data generated at T401 is completed, the calculation processing part 216 requests the digital camera 101a to transfer second image data generated at the timing T404. When the transfer of the second image data starts, the calculation processing part 216 directs the image data storing part 211 to store the data and simultaneously starts an image data transfer monitoring timer indicated by T405. When the transfer of the second image data is completed, the calculation processing part 216 compares image generation time data included in the image data with image sense time information included in the information correlating with image sensing. When a difference between the two pieces of time information is within an allowable range, it is recognized that the generated image data and the information correlating with image sensing are related to the second image sensing. The image data and the second information correlating with image sensing are combined with each other and the file creation is executed by the image file creating part 213. The subsequent operation is performed as described above. Thus, even when the transfer time of the image data exceeds the image sense interval, it is possible to surely match between the image data and the information correlating with image sensing and to perform error detection. FIG. 8 shows content processed by the image file creating part 213, which is an example in which a file is created from transferred image data 802 and transferred information correlating with image sensing 803 and displayed on a display of the personal computer 102 as indicated by reference numeral 801.

Figure 5:
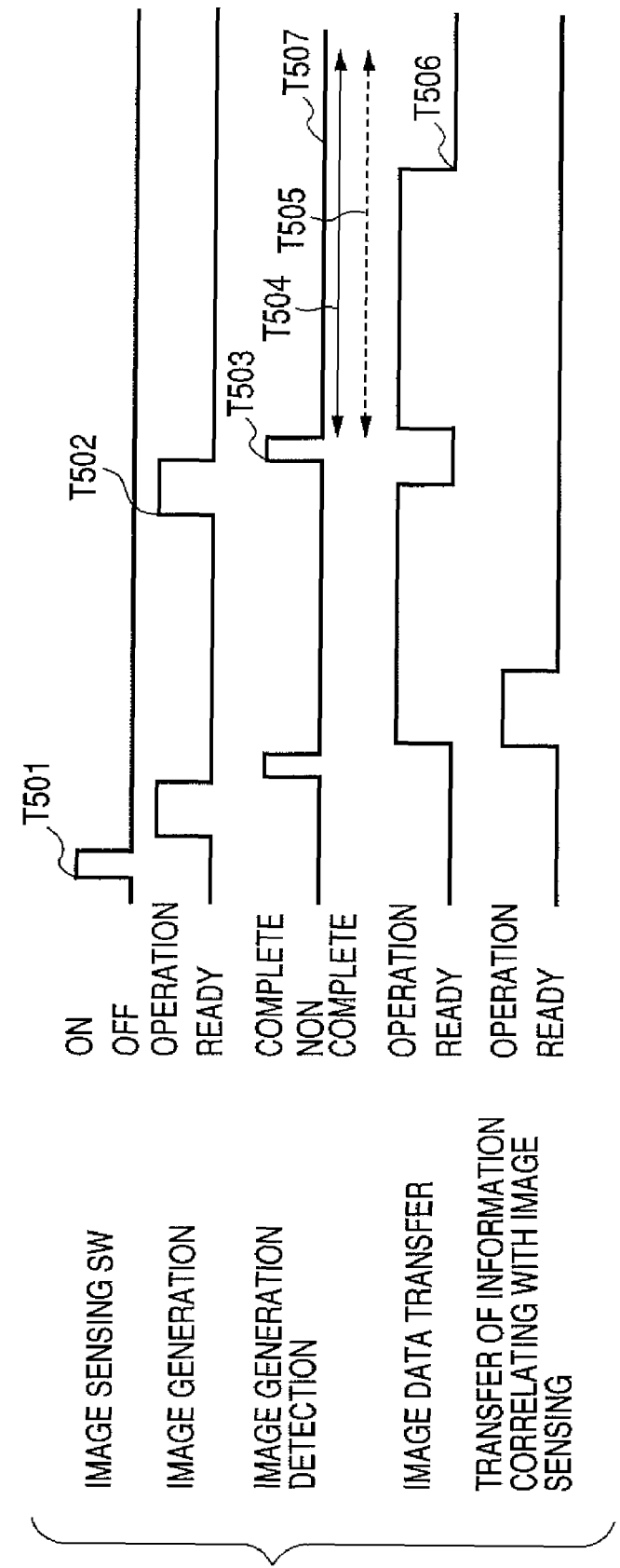
FIG. 5 is a timing chart showing image sensing operation.
Figure 9:
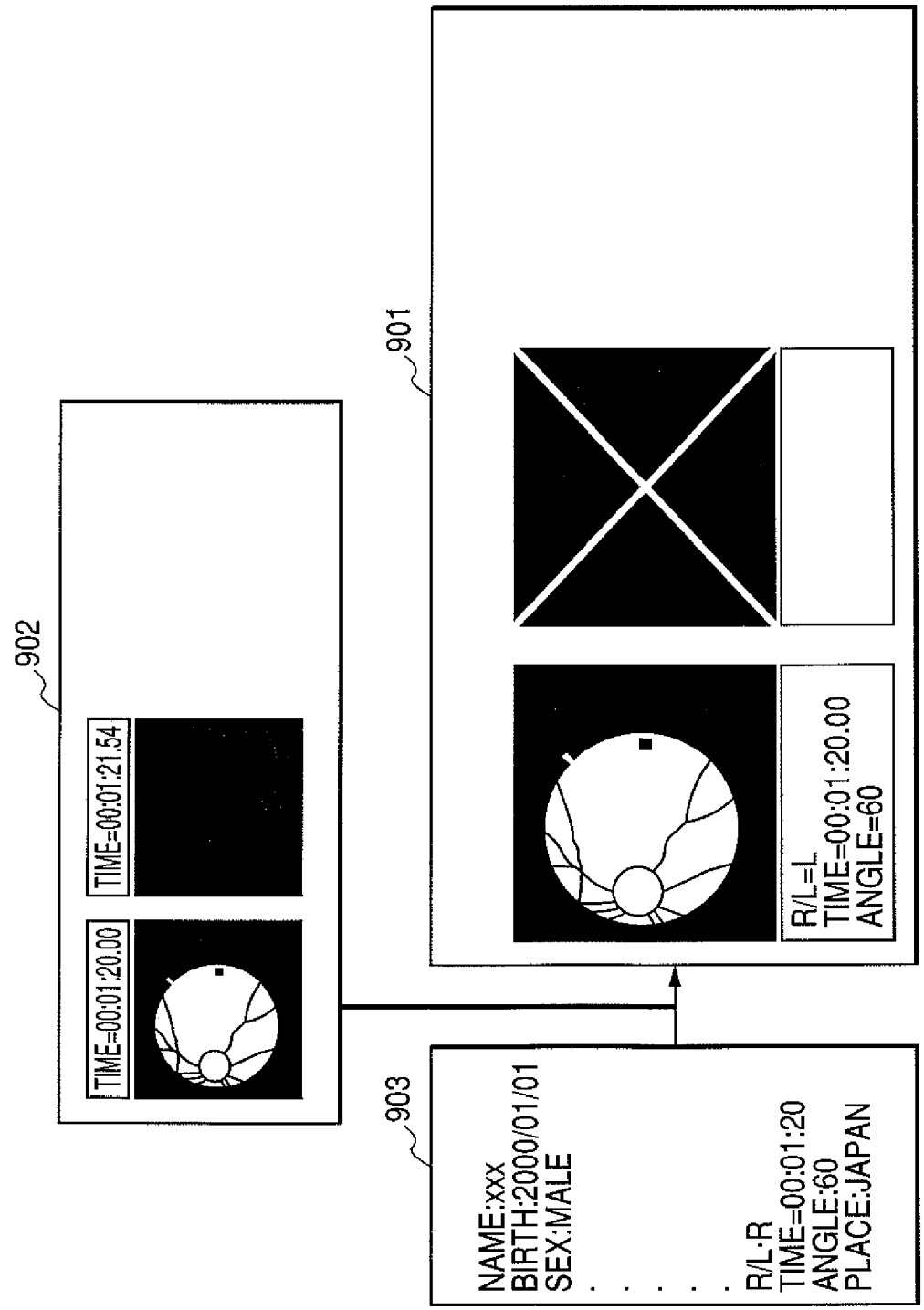
FIG. 9 is a view showing transfer data and displayed images.

FIG. 5 shows an error example in which the image data and information correlating with image sensing are not matched. Normal image sensing is performed at T501 and normal operation is performed in the procedures described earlier. Next, assume that the operator carelessly presses the image sensing switch 202 provided in the digital camera 101a at T502. Even when the image sensing switch 202 is pressed, the image is generated in the digital camera 101a as in the above-mentioned case. The calculation processing part 216 of the personal computer 102 detects image generation at a timing of T503, and starts a timer T504 and simultaneously requests the digital camera 101a to transfer the image data. However, the image sensing start switch 101b of the mydriatic type eye fundus camera 101 is not pressed. Therefore, the mydriatic type eye fundus camera 101 does not recognize the image sensing operation, so the acquisition of the information correlating with image sensing and the transfer thereof are not performed. Here, although the transfer of the image data is completed at T506, the transfer of the information correlating with image sensing is not started, so the timer T504 does not stop. The calculation processing part 216 recognizes an improper image at a timing T507 when the timer T504 elapsed a set timeout T505 and directs the alarm generation means 217 to generate an alarm. FIG. 9 shows an example of an alarm method. The second image sensing is performed without the operation of the mydriatic type eye fundus camera 101 and an acquired image does not include the image of the eye to be examined. Thus, the alarm generation means 217 sets a mark "x" on the improper image as indicated by reference numeral 901 to give to the operator an alarm indicating that it is an image acquired by improper operation.

In the description in FIG. 5, the detection is performed based on the timeout from T503. Alternatively, a pattern in which the information correlating with image sensing can be constantly obtained earlier than the image data may be used as an acquiring pattern. In the case where the information correlating with image sensing is not obtained at the time T506 when the transfer of the image data is completed without starting the timer, that is, in the case where an acquiring state is different from a predetermined pattern, an error may be recognized.

Figure 6:
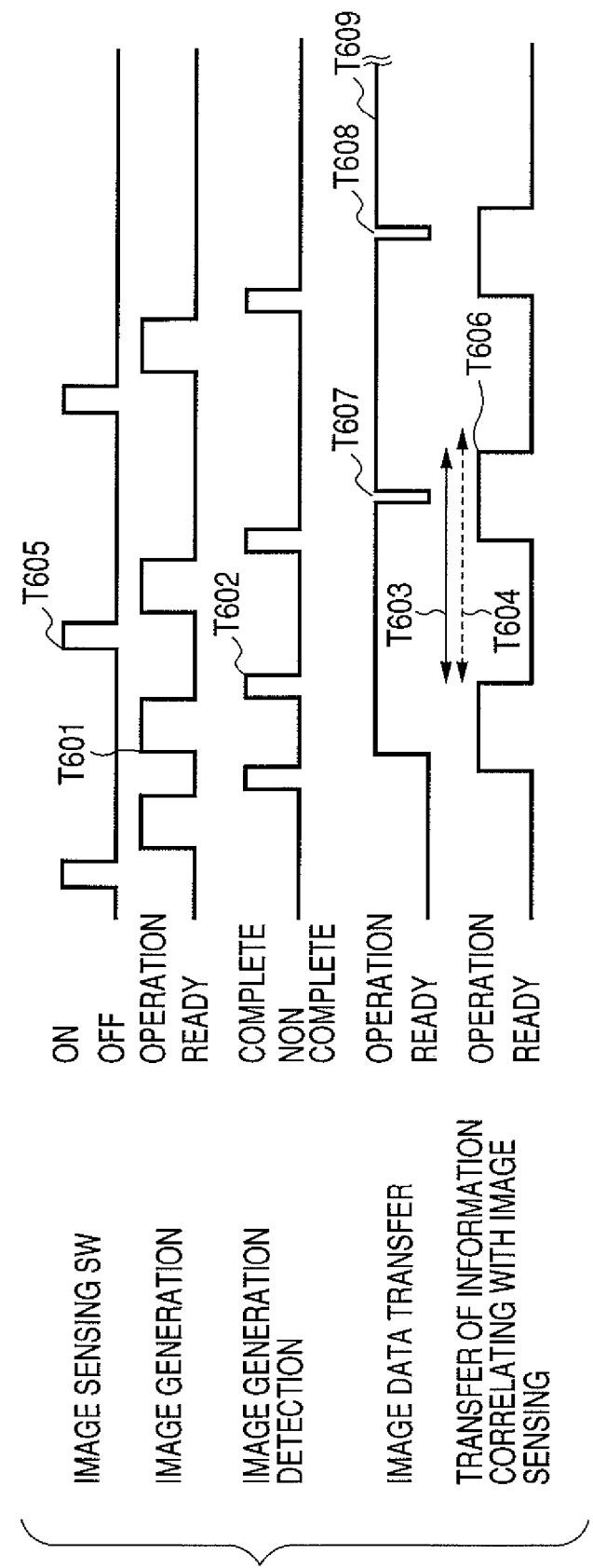
FIG. 6 is a timing chart showing image sensing operation.
Figure 10:
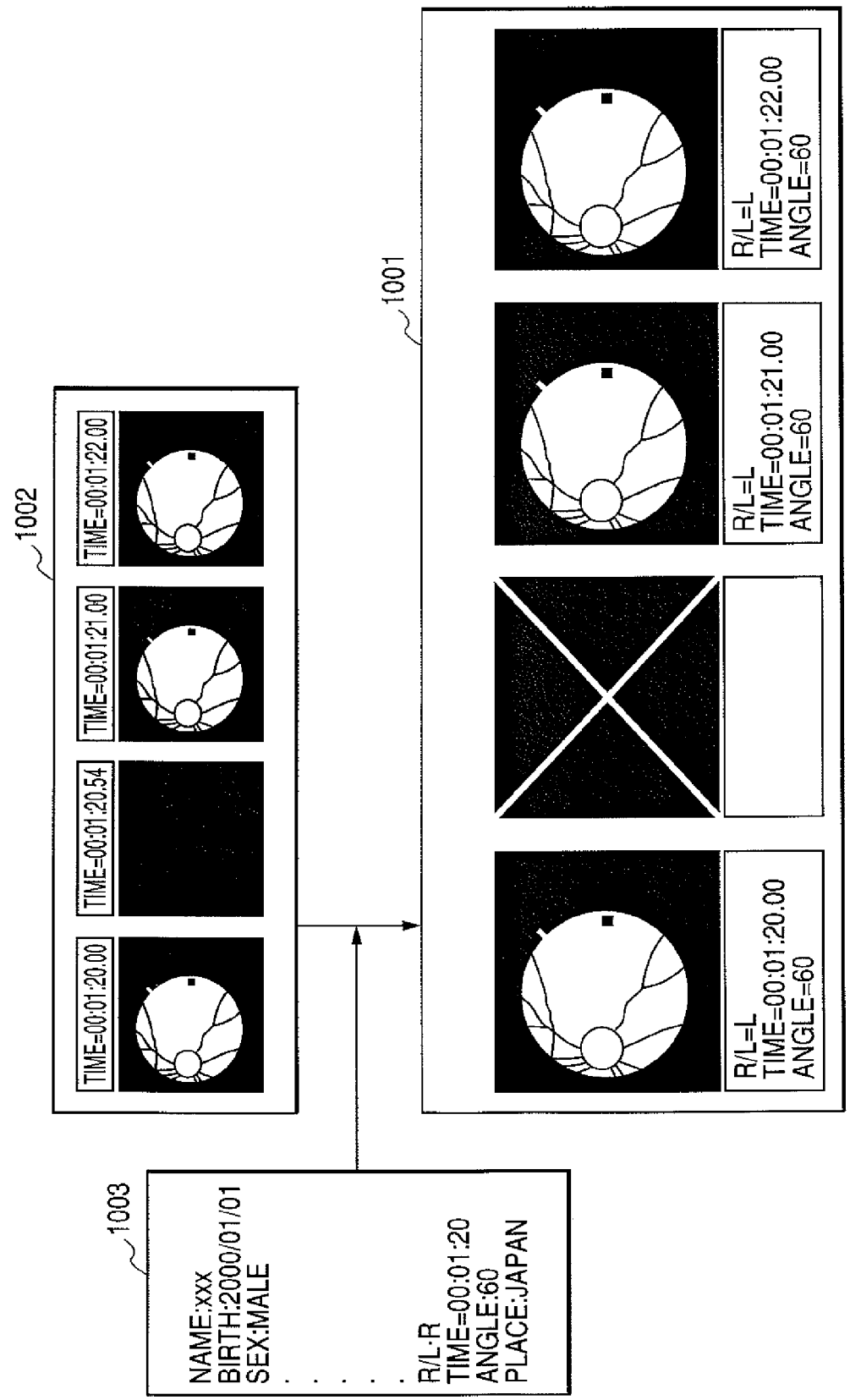
FIG. 10 is a view showing transfer data and displayed images.

Next, the description will be made with reference to FIG. 6. FIG. 6 shows the continuous image sensing such as the fluorescent image sensing as in the case shown in FIG. 4, which is an example in which an unexpected remote image sense instruction is issued to the digital camera at a timing indicated by T601 by, for example, noise entering from an outside. The calculation processing part 216 of the personal computer 102 detects image generation at T602 and starts a timer T603. Then, when the timer exceeds a timeout set period T604 with respect to the information correlating with image sensing from the mydriatic type eye fundus camera 101, as described in FIG. 5, the error can be detected. However, next image sensing operation is properly performed by the mydriatic type operator at a timing T605, so the acquisition of the information correlating with image sensing is completed at a timing of T606. Therefore, it is impossible to detect a timeout error of the information correlating with image sensing. Next, the transfer of image data which is erroneously generated and acquired is started at T607 and completed at T608. When the transfer is completed at T608, the calculation processing part 216 checks an image generation time included in the image data and then compares the image generation time with image sense time information included in the information correlating with image sensing. Here, it is recognized that the image data which is erroneously generated and acquired is an image generated before the image sensing is performed by the mydriatic type eye fundus camera 101, that is, the improper image. In the continuous image sensing such as the fluorescent image sensing, when the image sensing operation is interrupted by an error, the operationality significantly reduces. Therefore, the calculation processing part 216 continues the acquiring operation without interruption. Next, the image data generated by the image sensing at T605 is acquired by the transfer at T609 and it is checked to match between generation time information included in the image data and an image sense time of the information correlating with image sensing at T606. In the same procedures as described above, an image file is created from the image data and the information correlating with image sensing which are matched with each other. The subsequent acquisition of the image data and the information correlating with image sensing continues. When the improper image is recognized, the calculation processing part 216 causes the alarm generation means 217 to generate an alarm. FIG. 10 shows an example of a method of displaying the alarm. This indicates a state in which a second image is the improper image which is erroneously acquired and other images are properly acquired. According to the above-mentioned procedures, it is possible to detect the improper image which is erroneously generated and acquired during the continuous image sensing and to surely correlate the image data with the information correlating with image sensing during the image sensing.

Figure 7:
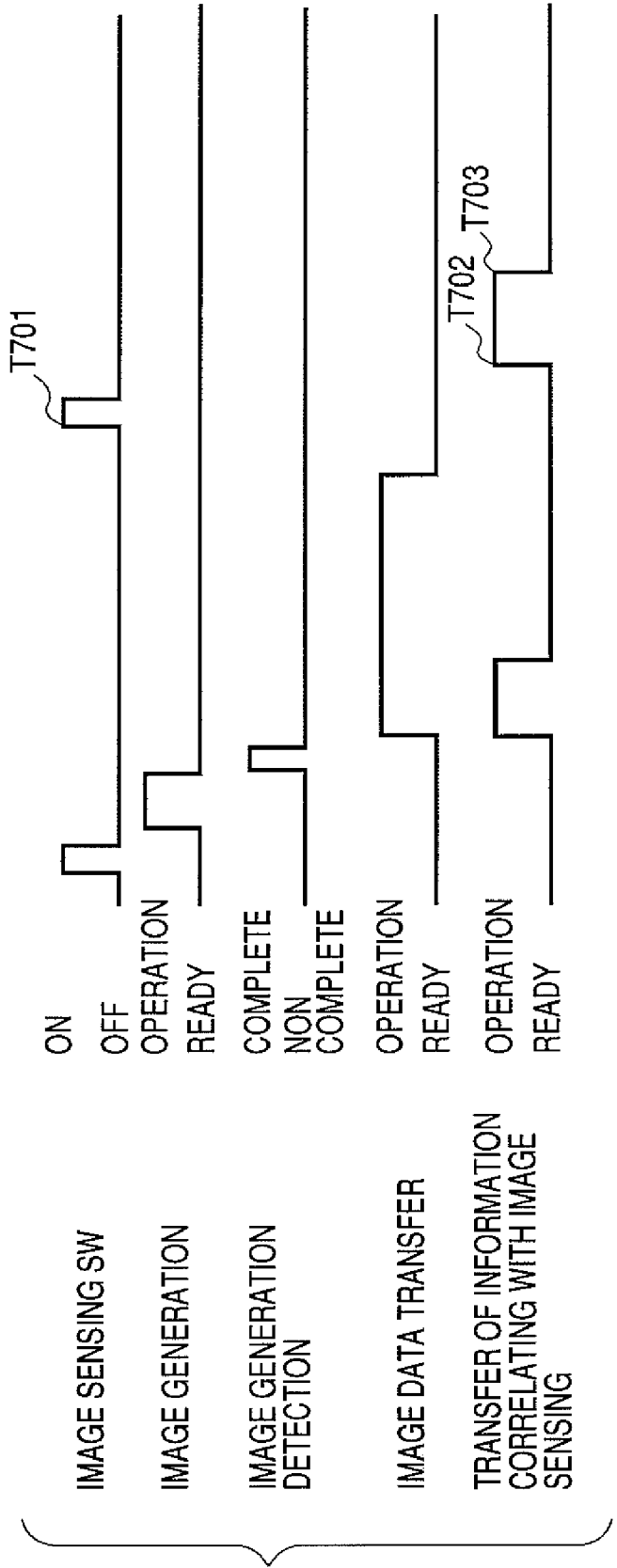
FIG. 7 is a timing chart showing image sensing operation.

A timing chart of FIG. 7 shows a state in which the second image sensing operation starts at a timing of T701 but a remote image sense instruction cannot be given to the digital camera 101a because of the failure of a control path for the digital camera 101a. In this case, although the second image sensing operation is performed, the image is not generated and thus the image generation is not detected. However, this cannot be recognized by the mydriatic type eye fundus camera 101, and the transfer of the information correlating with image sensing starts at a timing of T702. When the transfer of the information correlating with image sensing is completed at T703 in a state in which the image generation is not detected, the calculation processing part 216 recognizes that an output order is different from a predetermined pattern and directs the alarm generation means 217 to generate an alarm. In this case, the image data does not exist, so it is expected to display, for example, an alarm "the image is not transferred from the digital camera 101a. Please check the digital camera 101a". A monitoring timer may be started at the timing of T702. Then, when the acquisition of the image data is not completed within a predetermined time period, an error may be recognized.

As described with reference to FIGS. 3 to 7, even when the image data transfer time is longer than the image sense interval, the image data and the information correlating with image sensing can be accurately linked with each other. Even when the improper image is generated during the image sensing, the alarm can be accurately generated without the interruption of image sensing.

In the case where the improper image can be clearly determined as described with reference to FIGS. 5, 6, and 7, when a function in which the improper image is not stored in the image file storing unit 214 is further provided, the improvement of operationality and the saving of an unnecessary capacity of a recording medium can be achieved.

In this embodiment, the alarm to the improper image is mainly described. The checking alarm to the digital camera 101a as shown in FIG. 7, an alarm to the mydriatic type eye fundus camera 101 based on a detected defect of the information correlating with image sensing or a detected transfer error, and an alarm to a communication path may be generated.

In this embodiment, the filing system using the mydriatic type eye fundus camera in which an effect obtained by the present invention in the time of the continuous image sensing is large has been described. It is apparent that the present invention can be applied to a mydriatic type eye fundus camera having the same structure as described above.

As described above, according to the ophthalmologic image recording apparatus in this embodiment, even when the transfer of the image data is not completed before next image sensing, the sensed image data and the information correlating with image sensing can be surely correlated with each other. Therefore, even in the case of the continuous image sensing such as the fluorescent image sensing, it is possible to manage patient IDs, sensed eyes, image sensing regions, and the like.

An improper image which is generated by the malfunction of the digital camera attached to the eye fundus camera, noise therefrom, the failure thereof, or the like can be detected using various methods, so it is possible to properly give to the operator the alarm related to the improper image without the interruption of image sensing. When the function in which the improper image is not stored is further provided, the storage capacity can be saved without the storage of an unnecessary image other than an eye fundus picture.

As described above, according to the present invention, it is possible to provide an ophthalmologic image recording apparatus in which an improper image which is not an eye fundus picture can be removed to correlate each image with information correlating with image sensing.

Note that the present invention can be applied to an apparatus comprising a single device or to system constituted by a plurality of devices.

Furthermore, the invention can be implemented by supplying a software program, which implements the functions of the foregoing embodiments, directly or indirectly to a system or apparatus, reading the supplied program code with a computer of the system or apparatus, and then executing the program code. In this case, so long as the system or apparatus has the functions of the program, the mode of implementation need not rely upon a program.

Accordingly, since the functions of the present invention are implemented by computer, the program code installed in the computer also implements the present invention. In other words, the claims of the present invention also cover a computer program for the purpose of implementing the functions of the present invention.

In this case, so long as the system or apparatus has the functions of the program, the program may be executed in any form, such as an object code, a program executed by an interpreter, or scrip data supplied to an operating system.

Example of storage media that can be used for supplying the program are a floppy disk, a hard disk, an optical disk, a magneto-optical disk, a CD-ROM, a CD-R, a CD-RW, a magnetic tape, a non-volatile type memory card, a ROM, and a DVD (DVD-ROM and a DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a WWW (World Wide Web) server that downloads, to multiple users, the program files that implement the functions of the present invention by computer is also covered by the claims of the present invention.

It is also possible to encrypt and store the program of the present invention on a storage medium such as a CD-ROM, distribute the storage medium to users, allow users who meet certain requirements to download decryption key information from a website via the Internet, and allow these users to decrypt the encrypted program by using the key information, whereby the program is installed in the user computer.

Besides the cases where the aforementioned functions according to the embodiments are implemented by executing the read program by computer, an operating system or the like running on the computer may perform all or a part of the actual processing so that the functions of the foregoing embodiments can be implemented by this processing.

Furthermore, after the program read from the storage medium is written to a function expansion board inserted into the computer or to a memory provided in a function expansion unit connected to the computer, a CPU or the like mounted on the function expansion board or function expansion unit performs all or a part of the actual processing so that the functions of the foregoing embodiments can be implemented by this processing.

As many apparently widely different embodiments of the present invention can be made without departing from the spirit and scope thereof, it is to be understood that the invention is not limited to the specific embodiments thereof except as defined in the appended claims.

This application claims priority from Japanese Patent Application No. 2004-211688 filed on Jul. 20, 2004, which is hereby incorporated by reference herein.

The invention claimed is:

1. An ophthalmologic image recording apparatus for recording images of an eye to be examined, the apparatus comprising:
   (a) image sensing means for sensing and forming an image of the eye;
   (b) acquiring means for acquiring
      (i) through a first communication line, a plurality of images of the eye sensed by the image sensing means and image formation times, the image formation times constituting time information relating to times at which each of the plurality of images, respectively, was formed in the image sensing means, and
      (ii) through a second communication line, a plurality of image sensing correlation information sets, each respective information set relating to image sensing conditions for a corresponding one of the plurality of images and including an image sensing time;
   (c) control means for correlating each of the plurality of images with corresponding ones of the plurality of image sensing correlation information sets, wherein an image is correlated with an information set when a difference between the image formation time of the image and the image sensing time of the information set is within a predetermined range; and
   (d) recording means for recording a new file including a correlated image and information set.

2. An ophthalmologic image recording apparatus according to claim 1, wherein the control means comprises alarm means for generating an alarm when a difference between the image formation time of an image and the image sensing time of a corresponding information set exceeds the predetermined range.

3. An ophthalmologic image recording apparatus according to claim 1, wherein the control means measures an elapsed time from a time at which the acquiring means acquires information through one of the first communication line and the second communication line to a time at which the acquiring means acquires information through the other one, and comprises alarm means for generating an alarm when the elapsed time exceeds a predetermined time period.

4. An ophthalmologic image recording apparatus according to claim 1, wherein the control means monitors an acquiring order of information through the first communication line and the second communication line, and alarm means for generating an alarm when a monitoring result is different from a predetermined information acquiring pattern.

5. An ophthalmologic image recording method for recording images of an eye to be examined, the method comprising:

a first acquiring step of acquiring, through a first communication line, a plurality of sensed images of the eye and image formation times, the image formation times constituting time information relating to respective times at which each of the plurality of images was formed;

a second acquiring step of acquiring, through a second communication line, a plurality of image sensing correlation information sets, each respective information set relating to image sensing conditions for a corresponding one of the plurality of images and including an image sensing time;

a control step of correlating each of the plurality of images, with corresponding ones of the plurality of image sensing correlation information sets, wherein an image is correlated with an information set when a difference between the image formation time of the image and the image sensing time of the information set is within a predetermined range; and a recording step of recording a new file including a correlated image and information set.

6. A computer readable medium storing a program for causing a computer to perform an ophthalmologic image recording method for recording images of an eye to be examined, the medium including executable code for causing a computer to perform the following steps:

a first acquiring step of acquiring, through a first communication line, a plurality of sensed images of the eye and image formation times, the image formation times constituting time information relating to respective times at which each of the plurality of images was formed;

a second acquiring step of acquiring, through a second communication line, a plurality of image sensing correlation information sets, each respective information set relating to image sensing conditions for a corresponding one of the plurality of images and including an image sensing time;

a control step of correlating each of the plurality of images with the corresponding ones of the plurality of image sensing correlation information sets, wherein an image is correlated with an information set when a difference between the image formation time of the image and the image sensing time of the information set is within a predetermined range; and a recording step of recording a new file including a correlated image and information set.

* * * * *